(12) United States Patent
Javitt

(10) Patent No.: US 12,005,035 B1
(45) Date of Patent: Jun. 11, 2024

(54) COMPOSITIONS AND METHODS FOR TREATMENT OF CHRONIC PAIN AND DEPRESSION

(71) Applicant: Daniel C. Javitt, Ft. Lee, NJ (US)

(72) Inventor: Daniel C. Javitt, Ft. Lee, NJ (US)

( * ) Notice: Subject to any disclaimer, the term of this patent is extended or adjusted under 35 U.S.C. 154(b) by 0 days.

(21) Appl. No.: 18/448,990

(22) Filed: Aug. 14, 2023

(51) Int. Cl.
| | | |
|---|---|---|
| *A61K 31/135* | (2006.01) | |
| *A61K 31/167* | (2006.01) | |
| *A61K 33/00* | (2006.01) | |
| *A61P 25/04* | (2006.01) | |
| *A61P 25/24* | (2006.01) | |

(52) U.S. Cl.
CPC .......... *A61K 31/135* (2013.01); *A61K 31/167* (2013.01); *A61K 33/00* (2013.01); *A61P 25/04* (2018.01); *A61P 25/24* (2018.01)

(58) Field of Classification Search
CPC .... A61K 31/135; A61K 13/167; A61K 33/00; A61P 25/04; A61P 25/24
See application file for complete search history.

(56) References Cited

U.S. PATENT DOCUMENTS

| | | | |
|---|---|---|---|
| 2014/0275277 A1* | 9/2014 | Basstanie | A61K 47/26 |
| | | | 514/646 |
| 2021/0186896 A1* | 6/2021 | Becker | A61K 9/08 |
| 2022/0193000 A1* | 6/2022 | Tang | A61K 47/14 |

* cited by examiner

*Primary Examiner* — Robert A Wax
*Assistant Examiner* — Quanglong N Truong
(74) *Attorney, Agent, or Firm* — JMB Davis Ben-David

(57) ABSTRACT

Described herein is a composition that includes an N-methyl-D-aspartate receptor (NMDAR) antagonist and a TAS2R receptor response mediating agent for treating neuropathic pain and depression. Methods for treating chronic pain with the described composition are also described.

20 Claims, 4 Drawing Sheets

COMPOSITIONS AND METHODS FOR TREATMENT OF CHRONIC PAIN AND DEPRESSION

FIELD

Provided herein is a composition that includes an N-methyl-D-aspartate receptor (NMDAR) antagonist and a TAS2R receptor functional agonist for treating neuropathic pain and depression. Methods for treating chronic pain with the described composition are also described.

BACKGROUND

Acute pain may be considered a normal sensation triggered in the nervous system that serves to alert the individual to possible injury. By contrast, chronic (neuropathic) pain is a persistent discomfort in which pain signals persist for prolonged periods of time (e.g., weeks, months, or years). Neuropathic pain may be initiated by any of a number of instigating events, including trauma, infection, nerve injury or other physical events. However, neuropathic pain can occur even in the absence of an inciting event. Chronic (neuropathic) pain is also highly co-morbid with depression and may be both a cause and consequence. Both acute and persistent neuropathic pain are major public health problems that are associated with reduced quality of life, neuropsychiatric disorders such as depression, and increased opioid abuse. Current treatments for both acute and neuropathic pain are only partially effective.

Both acute and neuropathic pain may be modeled in rodents using the formalin test, in which formalin is injected into the hind paw of a rodent and the amount of subsequent licking behavior is used as an index of pain response.

The pain response in the formalin test is biphasic. In the initial acute period, corresponding to the first approximately 10 minutes following injection, the observed increased licking behavior is likely due to axially activated primary afferent nerve terminals. These changes are thought to be mediated by activation of the transient receptor potential ankyrin 1 (TRPA1) channels (e.g. Doncheva et al., 2018, Advances in Clinical and Experimental Medicine. 28. 10.17219/acem/94143).

The second phase of the formalin test, lasting from about 10-40 minutes, is thought to reflect the central sensitization of neurons in the dorsal horn and peripheral sensitization of nociceptors by formalin-induced local inflammatory response, suggesting that critical targets for treatment may be located with spinal cord and brain.

Neuropathic pain is a major contributor to development of additional neuropsychiatric disorders including depression. In addition to physical pain, other contributors to depression include adverse life experience, childhood abandonment, loss, bereavement and acute and chronic stress, or other forms of psychic pain.

The N-methyl-D-aspartate receptor (NM DAR) has been implicated in the maintenance of neuropathic pain, especially within central regions. For example, in prior studies, acute intraperitoneal administration of the NMDAR antagonist ketamine has been shown to block only the acute stages of formalin-induced pain following systemic administration, whereas it selectively blocks the late phase of the response following intrathecal administration (e.g. Bulutcu et al., Life Sci. 71:841-53, 2002). Other NMDAR antagonists that may have a ketamine-like effect include dextromethorphan, D-methadone, phencyclidine, S-ketamine and R-ketamine.

At a mechanistic level, maintenance of pain may be mediated by NMDAR-mediated Ca flow in spinal cord neurons leading to translocation of Protein kinase C (PKC) within the spinal cord (Yashpal et al., Pain 94:17-29, 2001). Ketamine produces its molecular effects by blocking $Ca^{2+}$ flow through NMDAR.

Ketamine has also been proposed as a treatment for chronic pain. However, findings have been mixed, and ketamine is not currently approved by the FDA for this purpose. Thus, there is a continuing need for compositions that can treat chronic pain, including chronic pain related to or resulting from neuropsychiatric conditions such as depression.

SUMMARY

Described herein is a pharmaceutical formulation that includes ketamine, including racemic ketamine and its enantiomers S-ketamine and R-ketamine, and a bitter taste receptor (TAS2R) response mediating agent, such as NaOH and denatonium, wherein the ketamine is provided at a concentration of between 100 μM and 100 mM, inclusive, and wherein the molar ratio of ketamine to TAS2R response mediating agent is between 10:1 and 1:5. These ratios may also be expressed as molar ratios of NaOH:ketamine or denatonium:ketamine.

In particular embodiments, the TAS2R response mediating agent is NaOH, and the molar ratio of ketamine to NaOH is 2:1.

In other embodiments, the TAS2R response mediating agent is denatonium, and the molar ratio of ketamine to denatonium is 1:5.

In still other particular embodiments, the described formulation includes 100 μM ketamine and 0.5 mM denatonium.

In particular embodiment, the formulation is formulated for parenteral administration, such as for subcutaneous, intramuscular, intravenous, intraarticular, intraperitoneal, or intrathecal administration.

Also described herein are methods of treatment, which are inclusive of uses of the described composition for treatment, of neuropathic (chronic) pain and/or depression associated with or developing from the chronic pain.

The methods of treatment of chronic pain and/or depression include administering to a subject in need thereof, an effective amount of any one of the described pharmaceutical formulations, thereby treating the chronic pain or chronic pain associated with depression.

In particular embodiments, the formulation is administered parenterally, such as subcutaneously, intramuscularly, intravenously, intraarticularly, intraperitoneally, or intrathecally.

In particular embodiments, the formulation is administered as a single bolus. In other particular embodiments, the formulation is administered as a gradual infusion over a series of minutes or even hours.

In some embodiments, the depression is major depression. In other embodiments, the depression is bipolar depression.

Given strong links between neuropathic pain and depression, the present invention will be effective not only in treatment of neuropathic pain, but also depressive disorders specifically, and neuropsychiatric disorders more generally.

The foregoing and other objects, features, and advantages will become more apparent from the following detailed description, which proceeds with reference to the accompanying figures.

DETAILED DESCRIPTION

Terms

Figure 1:
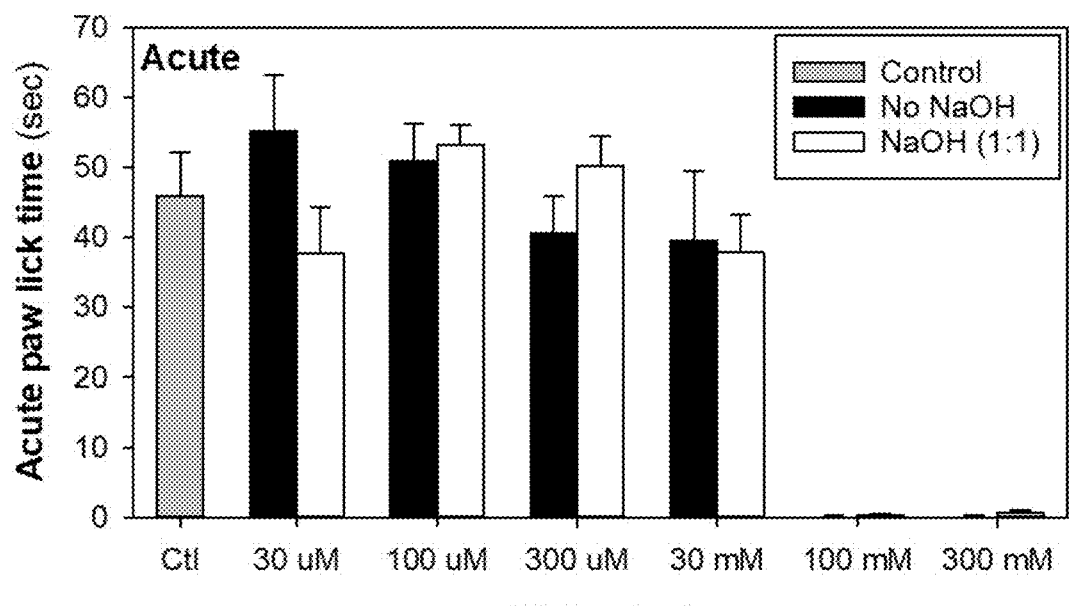
FIG. 1 shows the effects of increasing concentrations of ketamine or ketamine plus NaOH on the acute (top panel) or chronic (bottom panel) pain response. As indicated, NaOH was provided at an equimolar concentration as ketamine.
Figure 1:
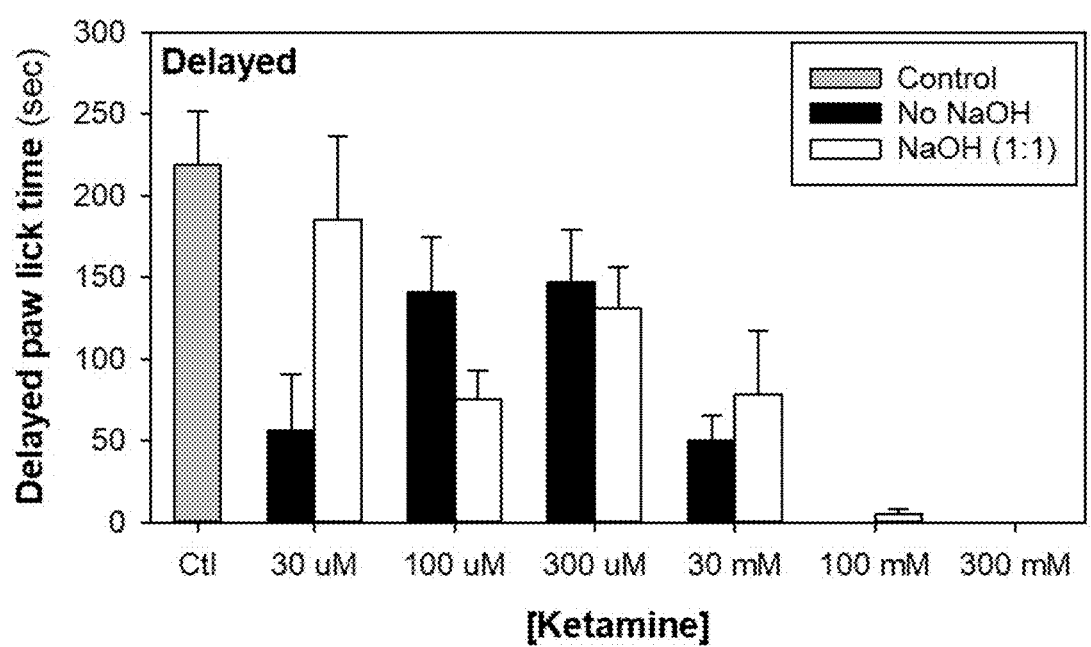

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The term "consists essentially of" or "consisting essentially of" indicates that the active ingredient or step of the described composition or method includes only the expressly recited ingredient or step. It is to be understood that compositions that "comprise" a given ingredient can also in other embodiments "consist essentially of" that ingredient. Similarly, methods that "comprise" a given set of steps can also in other embodiments "consist essentially of" the expressly indicated set of steps. The abbreviation, "e.g.," is derived from the Latin exempli gratia, and is used herein to indicate a non-limiting example. Thus, the abbreviation "e.g.," is synonymous with the term "for example."

In case of conflict, the present specification, including explanations of terms, will control. All materials, methods, and examples are illustrative and not intended to be limiting.

Administration: The introduction of a composition into a subject by a chosen route. Administration of an active compound or composition, including pharmaceutical formulations can be by any route known to one of skill in the art for providing the composition to a patient. Local administration of the described compositions includes direct administration to a target area. Examples of local administration also include, but are not limited to, topical administration, subcutaneous administration, intramuscular administration, intrathecal administration. As noted, local administration includes routes of administration typically used for systemic administration, for example by directing intravascular administration to the arterial supply for a particular organ. Systemic administration includes any route of administration designed to distribute an active compound or composition widely throughout the body via the circulatory system, including typical parenteral routes of administration. Thus, systemic administration includes, but is not limited to intra-arterial and intravenous administration. Systemic administration also includes, but is not limited to, topical administration, subcutaneous administration, intramuscular administration, or administration by inhalation, when such administration is directed at absorption and distribution throughout the body by the circulatory system.

Animal: Living multi-cellular vertebrate organisms, a category that includes, for example, mammals and birds. The term mammal includes both human and non-human mammals. Similarly, the term subject or patient includes both human and veterinary subjects or patients, who are in need of treatment for a particular condition, such as chronic pain and/or chronic pain associated with depression.

Effective amount of a compound, therapeutically effective amount of a compound: A quantity of compound sufficient to achieve a desired effect in a subject being treated. An effective amount of a compound can be administered in a single dose, or in several doses, for example daily, during a course of treatment. However, the effective amount of the compound will be dependent on the compound applied, the subject being treated, and particularly factors such as subject weight and metabolism, the severity and type of the affliction, and the manner of administration of the compound. It will be understood that the pharmaceutical formulations described herein are provided to patients in need of treatment at therapeutically effective amounts. In the combination therapies described herein, an "effective amount" of one component of the combination is the amount of that compound that is effective to provide the desired effect when used in combination with the other components of the combination.

Injectable composition: A pharmaceutically acceptable fluid composition comprising at least one active ingredient, although the compositions described herein comprise more than one active ingredient (i.e., and NMDAR antagonist and a TAS2R response mediating agent). The active ingredients are usually dissolved or suspended in a physiologically acceptable carrier, and the composition can additionally comprise minor amounts of one or more non-toxic auxiliary substances, such as emulsifying agents, preservatives, pH buffering agents and the like.

Pharmaceutically acceptable carriers and salts: The pharmaceutically acceptable carriers and pharmaceutically acceptable salts useful in this disclosure are conventional. Remington (The Science and Practice of Pharmacology, 22nd Edition (2012)), describes compositions and formulations suitable for pharmaceutical delivery of the compounds described herein. In general, the nature of the carrier and/or salt will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like.

Pharmaceutical agent: A chemical compound or composition capable of inducing a desired therapeutic or prophylactic effect when properly administered to a subject. As used herein the term "pharmaceutical composition" is understood to be synonymous with "pharmaceutical formulation."

Treating a disease: Treatment of a disease refers to a therapeutic intervention that ameliorates or reduces a sign or symptom of a disease or pathological condition after it has begun to develop, such as chronic pain.

NMDAR Antagonist Containing Compositions for Treatment of Chronic Pain

N-methyl-D-aspartate receptor (NMDAR) antagonists have previously been implicated in the maintenance of neuropathic pain. However, differences in the type of analgesia provided were observed to be dependent on the mode of administration. Although intraperitoneal administration of the NMDAR antagonist ketamine selectively blocked the acute stages of formalin-induced pain following systemic administration, it was observed to block the late (chronic) phase of the response following only intrathecal administration (e.g. Bulutcu et al., Life Sci. 71:841-53, 2002).

Ketamine produces its molecular effects by blocking Ca' flow through NMDAR. As demonstrated below, compounds that regulate intracellular Ca levels through bitter taste receptors (TAS2R), can act synergistically with ketamine or other NMDAR antagonists for treatment of chronic pain.

Accordingly, described herein are compositions, and specifically pharmaceutical formulations, that include a combination of an NM DAR antagonist and a TAS2R response mediating agent, which can treat chronic pain and chronic pain associated with depression.

NMDAR antagonists for use in the described composition include, but are not limited to ketamine, and NMDAR antagonist compounds having ketamine-like activity. Particular embodiments of such compounds include ketamine in its racemic form, its enantiomers S-ketamine and R-ketamine, dextromethorphan, and D-methadone.

Ketamine is typically formulated as Ketamine HCl (CAS Number 1867-66-9), and is marketed as a general anesthetic under the trade name Ketalar. Although the ketamine referred to in the examples provided herein is Ketamine HCl, it will be appreciated that Ketamine (CAS Number 6740-88-1) as well as other pharmaceutical forms of the compound, are encompassed by this disclosure. Ketamine (also termed R,S ketamine) is a racemic mixture of S- and R-ketamine. Ketamine as referred to in this application consists of the racemic mixture unless otherwise specified. Ketamine, S-ketamine, and R-ketamine are all reported to have anti-depressant effects either in humans or animal models. As demonstrated herein, these anti-depressant effects are maintained in the described combination compositions. Accordingly, in addition to the analgesic uses for the pharmaceutical compositions described herein, the described compositions can also be used for treatment of chronic pain as well as depression.

Ketamine may be administered orally, intranasally, or parenterally, and the described combinations can be formulated for such routes of administration. Parenteral routes include without limitation intravenous, intramuscular, subdermal, intrathecal, or subdural.

Ketamine is currently available for medical use at concentrations of 10, 50 and 100 mg/mL, corresponding to molar concentration of 42, 210 and 420 mM, based on a molecular weight of 237.7 g/mol (see e.g., pfizermedicalinformation.com/en-us/ketamine/storage-handling). However, as demonstrated herein, the concentration of ketamine in the described formulations necessary for treatment of chronic pain is significantly lower than that commonly administered. The formulations described herein include ketamine provided at a concentration from 100 µM to 100 mM (corresponding approximately to mass-based concentrations of 0.01 to 24 mg/mL), such as from 250 µM to 4 mM (corresponding to approximately 0.05 to 1 mg/mL).

In other particular embodiments, the formulations described herein include ketamine provided at a concentration from 30 µM to 100 mM, including 30 µM, 40 µM, 50 µM, 60 µM, 70 µM, 80 µM, 90 µM, 1 mM, 5 mM, 10 mM, 15 mM, 20 mM, 25, mM, 30 mM, 40 mM, 50 mM, 60 mM, 70 mM, 80 mM, 90 mM or 100 mM. Intermediate doses are possible as well. In still other embodiments, the described compositions include ketamine provided at a concentration from 30 µM to 30 mM.

The compositions described herein include as a second component a response mediating agent of at least one TAS2R. Bitter taste receptors (TAS2R) are an additional type of receptor that regulate intracellular Ca levels. Although these receptors were once thought to be localized only to the oral cavity and to be involved only in taste perception, the importance of extraoral TAS2Rs has been increasingly appreciated including receptors located within the central nervous system (e.g. Lu et a., J Gen Physiol, 149:181-197, 2017, DOI: 10.1085/jgp.201611637). For example, in bronchial smooth muscle, activation of TAS2R leads to dissociation of gustducin into βγ subunits, which, in turn, inhibits L-type voltage-dependent Ca2+ channels, leading to smooth muscle relaxation. Neurons in multiple regions of the rat brain have been shown to express TAS2Rs and downstream signaling molecules α-gustducin, PLCb2 and TRPM5 (e.g.Dehkordi et al., Brain Res 1475:1-10, 2012; DOI: 10.1016/j.brainres.2012.07.038), including regions potentially involved in pain perception and mood regulation. These include TAS2R4, which are expressed in rat neuronal cells (e.g. Singh et al., BBRC 406:146-151, 2011; D01:10.1016/j.bbrc.2011.02.016).

The human genome contains at least 47 different TAS2Rs, and are still being characterized. Many bitter compounds (TAS2R response mediating agent) bind to multiple TAS2R. Canonical ligands for TAS2R include compounds such as denatonium, quinine and quinidine. Quinidine and denatonium are among the most promiscuous compounds and activate 9 and 8 TAS2Rs, respectively. In the case of quinidine, receptors include TASR4, 7, 10, 14, 39, 40, 43, 44, and 46. In the case of denatonium, receptors include TAS2R4, 8, 10, 11, 13, 24, 39, 43, 46 and 47 may mediate the response to denatonium. The order of potency is TAS2R47>10>13/46>39>24/43>8.

In addition, and in general, alkali compounds have bitter taste and likely bind to TAS2R. Inorganic bases such as NaOH, KOH, or $MgOH_2$ may also have a bitter taste with presumed mediation through TAS2R. The cation may also contribute to the response (e.g. St. John & Boughter, Chem Senses 34:487-498, 2009). The identity of the TAS2R receptor that transduces the hydroxide effect has not been determined. Cations such as $Na^+$, when combined with a hydroxyl may also increase signaling through the TAS2R-linked TRMP5 channel. Interactions with other bitterness related proteins including but not limited to α-gustducin and PLCb2 could also be combined with an NMDAR antagonist as described.

The formulations described herein include at least one TAS2R response mediating agent. In particular embodiments, the TAS2R response mediating agent compound is a hydroxyl containing compound, combined with a cation. In some embodiments, the cation is sodium ($Na^+$). In some embodiments, the cation is calcium ($Ca^{2+}$). In some embodiments, the cation is combined with chloride to form a salt. Particular examples of the hydroxyl containing compound for use in the described combination formulations include NaOH, KOH, and $Ca(OH)_2$.

In another particular embodiment of the described formulations, the TAS2R response mediating compound is denatonium. In still further embodiments, bitter taste compounds for use in the described combination compositions can be identified from sources such as the BitterDB (available online at bitterdb.agri.huji.ac.il/dbbitter.php).

In particular embodiments of the described formulations, the NMDAR antagonist is ketamine, including its S- and R-ketamine, and the TAS2R response mediating compound is NaOH. In such embodiments, ketamine can be provided in the concentrations noted above, and NaOH is combined with ketamine at a molar ratio in the range of 1:10 to 1:1 NaOH to ketamine. Non-limiting examples include 1:10, 1:9, 1:8, 1:7, 1:6, 1:5, 1:4, 1:3, 1:2, and 1:1. Exemplary non-integer ratios of NaOH to ketamine that can be used in the described formulations include 1:2.1, 1:2.2, 1:2.3, 1:2.4, 1:2.5, 1:2.6, 1:2.7, 1:2.8, and 1:2.9. Similar non-integer ratios can be used between the noted integer ratios. In other embodiments, the range of NaOH to ketamine is between 1:5 and 1:1. In a particular embodiment, the ratio is NaOH to ketamine in the pharmaceutical formulation is 1:5. In still further embodiments, the ratio of NaOH to ketamine is 1:2.

In other particular embodiments of the described formulations, the NMDAR antagonist is ketamine and the TAS2R response mediating compound is denatonium. In such embodiments, ketamine can be provided in the concentrations noted above, and denatonium is combined with ketamine at a molar ratio in the range of 10:1 to 1:1 ketamine to denatonium. Non-limiting examples include 10:1, 9:1, 8:1, 7:1, 6:1, 5:1, 4:1, 3:1, 2:1, 1:1. Exemplary non-integer ratios of ketamine to denatonium that can be used in the described formulations include 1:5.1, 1:5.2, 1:5.3, 1:5.4, 1:5.5, 1:5.6, 1:5.7, 1:5.8, and 1:5.9. Similar non-integer ratios can be used between the noted integer ratios. In other embodiments, the range of ketamine to denatonium is between 1:5 and 1:1. In a particular embodiment, the ratio is ketamine to denatonium in the pharmaceutical formulation is 1:5.

The described pharmaceutical formulations are in particular embodiments formulated for parental administration to a patient. For example, for subcutaneous, intramuscular, intravenous, intraarticular, intraperitoneal, or intrathecal administration. Such formulations include pharmaceutically acceptable salts, buffers, solvents, excipients, and diluents common to the art. In some embodiments, the solution may be rendered partially or fully isotonic by addition of a NaCl solution. Examples of NaCl solutions that can be added to render the solution formulation of the described compositions include ⅓ normal, ½ normal, or ⅔ normal. An isotonic solution is defined as containing 0.9% NaCl.

Methods of Treating Chronic Pain and Chronic Pain Associated with Depression

Described herein is the observation that a parenterally administered composition of ketamine and a TAS2R response mediating agent such as NaOH or denatonium is effective at treating neuropathic (chronic) pain. In addition to treating chronic pain, ketamine-TAS2R combinations such as ketamine-NaOH and ketamine-denatonium were observed to be effective in treating the associated depressive symptoms. Many psychic factors may contribute to the risk for depression including childhood loss, bereavement, life change, stress, physical or sexual abuse, relationship difficulties or financial loss. These collectively are termed psychic pain. Manifestations of depression include sadness, tension, reduced sleep and appetite, difficulties in concentration, difficulty in starting activities, reduced interest, and pessimistic and suicidal thoughts. Treatment of chronic pain and associated depression can therefore also help ameliorate the long term effects of psychic pain.

Accordingly, the compositions described herein can be used in methods for treating chronic pain in a subject in need of such treatment. The methods include administering to a subject any one of the compositions (pharmaceutical formulations) described herein, thereby treating the chronic pain, and in particular embodiments the chronic pain and associated depression or depressive symptoms as noted above.

In particular embodiments, the described pharmaceutical formulation is administered parenterally, and so the formulation is adapted to the particular parental administration used. For example, in particular embodiments, the pharmaceutical formulation is administered subcutaneously, intramuscularly, intravenously, intraarticularly, intraperitoneally, or intrathecally. Accordingly, the described pharmaceutical formulation can, in particular embodiments, be administered by a systemic method of administration, and can, in other particular embodiments, be administered by a local method of administration. It will be appreciated that the described combination can be formulated as needed for a particular mode of administration, though the appropriate formulation for one type of administration can, in particular embodiments also be used for another type of administration.

In some embodiments, the provided pharmaceutical formulation is administered as a single bolus to the subject. In other embodiments, it is infused gradually over time periods of several minutes or hours. Non-limiting examples include 5, 10, 15, 20, 30, 40, 60, 90, 120 minutes or longer. Intermediate administration periods are contemplated as well.

In particular embodiments, the pharmaceutical formulation is provided within a treatment regimen that includes periodic administration of the pharmaceutical formulation of days, weeks, months, and periods in between, In particular embodiments, the formulation is provided over the course of regular periods, for example every five days or every two weeks. In other embodiments, the formulation is provided in a staggered manner. A non-limiting illustrative example of such staggered treatment is treatment every day for a week, followed by two weeks without treatment, followed by treatment every day for a week.

As noted, the described methods can treat neuropathic (chronic) pain, but also depression associated with or stemming from neuropathic pain. In particular embodiments the depression is major depression. In other embodiments, the depression is bipolar depression.

The following examples are provided to illustrate certain particular features and/or embodiments. These examples should not be construed to limit the disclosure to the particular features or embodiments described.

EXAMPLES

Example 1: Modulation of Analgesic Efficacy of Ketamine by NaOH in the Rat Formalin Test This example demonstrates the use of the formalin test to determine the potential analgesic effects of compounds for pain. In this test, effects are measured on both acute and delayed formalin-induced pain, as reflected in paw licking behavior.

Methods: All studies were performed at Psychogenics, Inc. (Tarrytown, NY). Male SD rats (Envigo) were used in the study. All rats were examined and weighed (about 200 g) prior to initiation of the study to assure adequate health and suitability. For the formalin test, rats were habituated for 30 min in observation chambers with cameras positioned underneath. After the pre-treatment time, animals received a subcutaneous injection into the plantar surface of the left hind-paw with 15 ul of 5% formalin using a Hamilton micro-syringe and a 30-gauge needle.

Rats were returned to the observation chamber and immediately observed for behavior. The total time spent licking, flinching or biting the treated hind-paw over the next 35 min was recorded and videos were scored by a trained observer blinded to the treatment group. The acute response was evaluated in 5 min intervals for 0-10 min, and the delayed response was evaluated from 10-35 or 10-40 min.

For this experiment, effects of ketamine alone vs. ketamine+NaOH were assessed at concentrations between 30 uM ($\mu$M) and 100 mM vs. control. Secondary analyses evaluated relative effects of ketamine+NaOH vs. ketamine alone. Analyses were performed by between-group t-tests or multiway ANOVA as expected. For each experiment, outliers ±2SD from the group means were removed from the analyses as flagged in study reports.

Results: Mean (sd) paw licking time for this experiment is shown in Table 1 and FIG. 1. Effects of all combinations of ketamine and NaOH were compared vs. control using one-way ANOVA across the 30, 100 and 300 $\mu$M doses. As expected, there were no significant treatment effects on acute pain response (F=1.185, df=6,105, p=0.32). By contrast, a significant cross-group effect was observed for the delayed response (F=2.656, df=6.95, p=0.02), with significant post-hoc differences vs. control only for the ketamine 30 $\mu$M dose in the absence of NaOH (p=0.004), but for the 100 $\mu$M (p<0.001) and 300 $\mu$M dose (p=0.042) in the presence of NaOH.

Effects of ketamine alone vs. ketamine+NaOH were compared by 2-way ANOVA with factors of ketamine concentration (30, 100, 300 $\mu$M) and absence/presence of NaOH. Neither the main effects of ketamine (F=0.55, df=2.77, p=0.58) or NaOH (F=0.32, df=1.57, p=0.57) were significant. However, the interaction effect between ketamine dose and absence/presence of NaOH was significant (F=3.60, df=2.77, p=0.032), reflecting significant modulation of ketamine effect by NaOH, such that ketamine was numerically less effective at the 30 $\mu$M dose in the absence vs. presence of NaOH, but more effective at the 100 and 300 $\mu$M dose in combination with NaOH.

At a concentration of 30 mM, effects of ketamine were significant both for ketamine alone and Ketamine NaOH. At concentrations of 30 mM, significant inhibition of delayed response was observed in both the absence and presence of NaOH (all p<0.005). At doses of 3.00 mM, significant effects were also observed on acute response (all p<0.001), suggesting non-specific behavioral effects.

Figure 2:
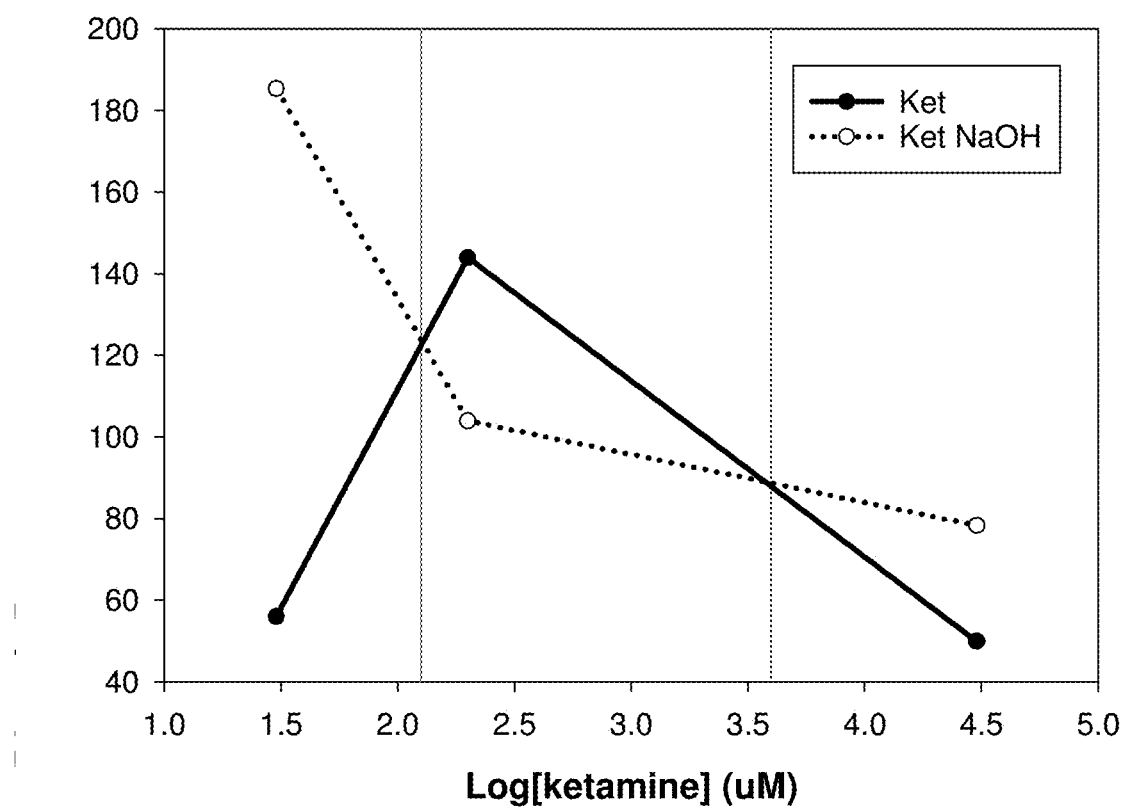
FIG. 2 shows a graphical analysis to confirm the optimal dose range of the effect of equimolar ketamine:NaOH combination on the delayed pain response.

In a graphical analysis to confirm the optimal dose range (FIG. 2), Ketamine NaOH reduced delayed paw licking activity over the interval of 2.1-3.6 log-$\mu$M ketamine, corresponding to concentrations of between 125 $\mu$M and 4.0 mM.

Conclusions: These findings demonstrate the superior analgesic effect towards chronic pain of a combination of ketamine and NaOH vs. ketamine alone at ketamine/NaOH concentrations of >30 $\mu$M to <30 mM, and particularly between 0.125 and 4 mM. The significant effect resulting from a combination of ketamine and NaOH is unanticipated from the prior literature.

TABLE 1

Paw licking time (sec) during the acute and chronic phase following formalin treatment in the absence and presence of ketamine and NaOH.

| Time interval Condition | N | Acute Mean | Std | N | Chronic Mean | Std | p vs. Ctl |
|---|---|---|---|---|---|---|---|
| Control | 18 | 46.00 | 25.70 | 19 | 218.47 | 144.96 | — |
| Ketamine 30 $\mu$M | 10 | 55.20 | 25.01 | 7 | 56.00 | 90.52 | .003 |
| Ketamine 100 $\mu$M | 20 | 50.95 | 23.52 | 17 | 140.71 | 138.14 | .11 |
| Ketamine 300 $\mu$M | 18 | 40.50 | 22.77 | 18 | 147.00 | 134.86 | .13 |
| Ketamine 30 mM | 9 | 39.44 | 29.98 | 8 | 49.88 | 42.39 | <.001 |
| Ketamine 100 mM | 9 | 0.11 | 0.33 | 7 | 0.00 | 0.00 | <.001 |
| Ketamine 300 mM | 9 | 0.11 | 0.33 | 10 | 0.00 | 0.00 | <.001 |
| Ketamine 30 $\mu$M + NaOH | 9 | 37.78 | 19.38 | 10 | 185.30 | 161.53 | .59 |
| Ketamine 100 $\mu$M + NaOH | 17 | 53.12 | 12.08 | 15 | 75.20 | 67.64 | <.001 |
| Ketamine 300 $\mu$M + NaOH | 20 | 50.25 | 18.74 | 16 | 130.75 | 101.33 | .044 |
| Ketamine 30 mM + NaOH | 10 | 37.90 | 16.74 | 8 | 78.25 | 110.00 | .014 |
| Ketamine 100 mM + NaOH | 8 | 0.25 | 0.71 | 7 | 5.29 | 6.32 | <.001 |
| Ketamine 300 mM + NaOH | 10 | 0.60 | 1.26 | 10 | 0.00 | 0.00 | <.001 |

NaOH was added at equimolar concentration to ketamine; Significance levels based on t-test; equal variances not assumed; BOLD=significantly different from control (p<0.05).

Example 2: Effects of Different Ratios of Ketamine Vs. NaOH on Analgesic Effects The previous example demonstrated a significant analgesic effect when an equimolar combination of ketamine and NaOH was provided in the rat formalin test. In this example the effects of different molar ratios of ketamine:NaOH were evaluated to test theories that a curvilinear relationship may be observed across doses.

Methods: Overall methods were the same as for Example 1. However, for this study, the concentration of ketamine was fixed at 100 $\mu$M across conditions, and the ratio of NaOH to ketamine was varied from 1:10 (0.1 ratio) to 1:2 (0.5 ratio) to 3:4 (0.75 ratio) to 1:1 (1.0 ratio). An ANOVA was conducted across ratios to determine statistical significance.

Figure 3:
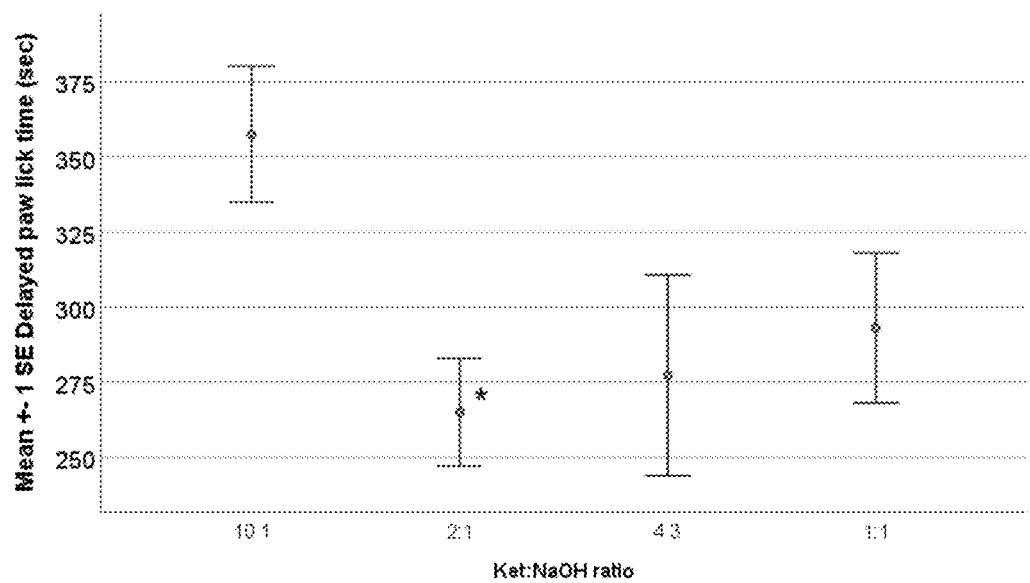
FIG. 3 shows the effect of different ratios of Ketamine (Ket):NaOH ratios±s.e.m. on delayed paw lick time. $*p<0.05$ vs. 10:1 ratio.

Results: Data are shown in Table 2 and FIG. 3. When delayed response was compared across NaOH/ketamine ratios, no significant difference was observed for the acute pain response (F=0.62, df=3.36, p=0.61). For the delayed pain response, a significant quadratic effect was observed across ratios (p=0.04), with ratios of 0.50 (p=0.014) and 0.75 (p=0.032) both producing significantly greater reduction in analgesic response than was observed at a ratio of 0.1, while a trend level difference was observed for a ratio of 1 (p=0.081).

Conclusions: These findings suggest that effects of NaOH are greatest when it is combined with ketamine at a ratio of 2:1 ketamine:NaOH. The finding of a ratio effect supports the initial findings from use of a 1:1 ratio combination (Experiment 1). Across all experiments, the delayed response in the presence of Ketamine 100 $\mu$M+NaOH 100

μM (1:1 ratio) was significantly different from control (saline) following control for experiment # (F=7.05, df=1.57, p=0.01).

TABLE 2

Effect of varying ketamine:NaOH ratio on delayed paw licking (sec)

| Ratio | N | mean | Std | p v.1 |
|---|---|---|---|---|
| .10 | 10 | 357.60 | 71.6 | — |
| .50 | 10 | 265.00 | 56.7 | 0.005 |
| .75 | 10 | 277.30 | 105.8 | 0.062 |
| 1.00 | 10 | 293.10 | 78.9 | 0.072 |

Example 3: Effects of High-Affinity TAS2R Antagonists

This example tested the hypothesis that TAS2Rs modulate the NMDAR-sensitive hyperalgesic response to inflammation. To this end, formalin tests were repeated in the absence and presence of 3 canonical TAS2R agonists: quinine, quinidine, and denatonium. We hypothesized that there would be a differential response across compounds, reflecting differential involvement of specific TAS2R types.

Methods: Formalin test methods were the same as for examples 1 and 2. Quinine HCl, Quinidine gluconate and Denatonium benzoate were all administered at doses of 0.5 mM. Denatonium was additionally administered combined with Ketamine 100 μM.

Results: Results are shown in Table 3. As in the previous examples, no significant effect was observed on the acute hyperalgesic response (F=0.17, df=3.36, p=0.92). By contrast, a significant effect was observed on the delayed hyperalgesic response (F=4.88, df=3.36, p=0.006), with denatonium benzoate producing a significant reduction in hyperalgesia vs. control (p=0.029).

Conclusions: These data provide the first evidence for reduction of neuropathic pain by a TAS2R agonist, and suggest a critical role of either local or central TAS2R receptors in the etiology of pain. The differential effect of denatonium vs. quinine/quinidine suggests involvement of specific TAS2Rs, such as potentially TAS2R47 that responds differentially to these compounds.

TABLE 3

Effect of putative TAS2R ligands on delayed hind paw licking (sec) (marginal means)

| Compound | N | Mean | Std. Error | P vs control | P vs. denatonium alone |
|---|---|---|---|---|---|
| Control | 20 | 2363 | 30.8 | — | |
| Quinine, .5 mM | 10 | 346.5 | 64.3 | .006 | |
| Quinidine, .5 mM | 10 | 288.6 | 100.6 | .30 | |
| Denatonium, .5 mM | 10 | 161.0 | 151.2 | .19 | |
| Ketamine 100 μM + Denatonium .5 mM | 10 | 50.6 | 66.6 | <001 | .056 |

Example 4: Effects of Other Compositions

In order to evaluate the specificity of the synergistic effect between ketamine and NaOH, formalin tests were evaluated in combination with other hydroxides, including $Ca(OH)_2$ and KOH. In addition, S-ketamine is reported to have anti-depressant effects similar to ketamine. Formalin tests were therefore conducted in the presence of 100 μM S-ketamine relative to racemic ketamine.

Results: Results are shown in Table 4. No significant effects were observed across conditions for either acute or delayed paw lick responses. As in earlier experiments, ketamine 100 μM did not significantly reduce delayed responses in the absence of NaOH. Neither $Ca(OH)_2$ or KOH enhanced the effects of ketamine 100 μM. S-Ketamine 100 μM induced numeric decreases in delayed paw licking vs. control, but the differences were not statistically significant.

Conclusions: Neither $Ca(OH)_2$ nor KOH reproduced the synergistic effects of NaOH when combined with ketamine. These results show an unexpected specific synergy between ketamine and NaOH in the treatment of chronic pain. S-Ketamine produced effects somewhat larger than racemic ketamine and may be a preferred NMDAR antagonist.

TABLE 4

Combinations of ketamine with other cations, and of S-ketamine

| | N | Acute Mean | SD | Chronic Mean | SD | p vs Control |
|---|---|---|---|---|---|---|
| Control | 10 | 53.2 | 19.3 | 198.3 | 159.0 | — |
| Ketamine 100 μM | 10 | 54.5 | 37.2 | 196.4 | 178.4 | 0.98 |
| Ket HCl 100 μM/CaOH | 9 | 40.2 | 21.2 | 157.7 | 84.2 | 0.49 |
| Ket HCl 100 μM/KOH | 10 | 55.6 | 31.1 | 157.3 | 132.8 | 0.54 |
| S-ketamine 100 μM | 10 | 50.5 | 31.2 | 120.6 | 115.4 | 0.23 |

Example 5: Effects of Combined Ketamine+NaOH on Depression-Related Behaviors

Chronic pain may also lead to depressive symptoms that cause additional disability and may reflect an independent treatment target. Anti-depression effects may be modeled in rodents using behavioral measures including the forced swim test, which measures the time that rodents remain immobile when placed in water. In one model, chronic pain Is created by spinal nerve ligation (SNL) in which a ligation is placed around the left L5 nerve, which leads to hypersensitivity of the paw withdrawal threshold.

Methods: Male Sprague Dawley rats (about 150 g on arrival) from Envigo were used. Upon receipt animals were group housed for the remainder of their stay at PsychoGenics. All animals were examined and weighed prior to initiation of the study to assure adequate health and suitability. During the study, 12/12 light/dark cycles were maintained. The room temperature was maintained between 20 and 23° C. with a relative humidity maintained around 50%. Chow and water were provided ad libitum for the duration of the study. Rats were single housed after surgery. The test was performed during the animal's light cycle phase.

Spinal nerve ligation: Under general anesthesia with continuous inhalation of isoflurane, surgery was performed with aseptic procedures. The skin at the area of the lower lumbar and sacral level of the animals is shaved and disinfected with betadine and alcohol. Sterile ophthalmic ointment was used to lubricate the eyes. Animals were observed continuously for the level of anesthesia, testing for the animal's reflex response to a tail or paw pinch and closely monitoring the animal's breathing. A heating pad was used to maintain body temperature at 37° C. while the animals recovered from anesthesia. A left longitudinal incision at the level next to the vertebral column was made and the left paraspinal muscles were separated. The transverse process of L6 was removed and nearby connective tissue cleaned to expose L5 and L6 spinal nerves. After the nerves were isolated and clearly visualized, 4-0 silk threads were used to ligate the left L5. The muscles were then sutured with 4-0 silk threads and the wound closed by staples. All rats received an analgesic (buprenorphine, 0.05 mg/kg, s.c.) immediately before and 6 hours after surgery. Each rat was monitored until awake and moving freely around the recovery chamber. Animals were then single-housed for the duration of the study.

Paw withdrawal test: Paw withdrawal from a mechanical stimulus was measured by applying VF filaments of ascending bending force to the plantar surface of the hind paws (ipsilateral and contralateral). Baseline and post-treatment withdrawal threshold values for non-noxious mechanical sensitivity were evaluated using von Frey filaments (Semmes-Weinstein filaments, Stoelting) of varying stiffness (0.4, 0.7, 1.2, 2.0, 3.6, 5.5, 8.5, 10, 15, 26 g) starting with the middle filament (3.6 g). Each filament was presented perpendicular to the plantar surface with sufficient force to cause slight buckling against the paw, then held for approximately 6 seconds or until a positive response was noted. A positive response was defined as withdrawal from the von Frey filament. Confirmation of threshold was tested by examining the filament above and below the withdrawal response in a modified up-down method paradigm. If a response was positive, the next descending filament was tested. If the response was negative, the next ascending filament was tested. Each filament was applied 3 times. The threshold responses from both hindpaws were recorded at each time point.

Forced swim test: The forced swim (FS) test is considered to predict anti-depression effects. When rats are forced to swim in a small cylinder from which no escape is possible, they readily adopt a characteristic immobile posture and make no further attempts to escape except for small movements needed to prevent them from drowning. The immobility is considered to reflect a 'depressive mood' in which animals cease to struggle to escape the aversive situation. FS tests commenced approximately 2 weeks post-surgery after rats had been balanced by their post-operative PWT. All experiments were carried out at ambient temperature under artificial lighting during the light cycle of the rat. Each Forced Swim chamber was constructed of clear acrylic (height=40 cm; diameter=20.3 cm). All rats were exposed to a swim test prior to compound administration. This pre-administration swim test consisted of one 15 min session in individual cylinders containing 23±1° C. water; this was followed 24 h later by the experimental test of 5 min. The water level was 16 cm deep during habituation and 30 cm deep during testing. Immobility, climbing, and swimming behaviors were recorded every 5 sec for a total of 60 counts per subject. In the event that an animal was unable to maintain a posture with its nose above water, it was removed immediately from the water and therefore eliminated from the study.

Figure 4:
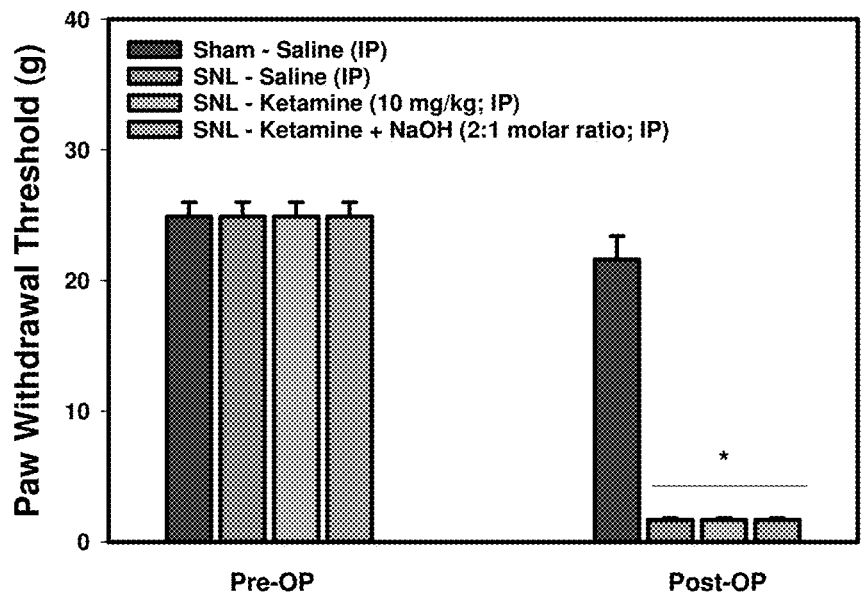
FIG. 4 shows the increase in acute pain sensitivity following spinal ligation (SNL) surgery in rodents. Animals before (Pre-OP) and after (Post-OP) surgery were tested. In all experimental conditions examined (saline, ketamine, 2:1 ketamine:NaOH), Post-OP animals demonstrated the expected induced increased chronic pain sensitivity as reflected in a significantly reduced paw withdrawal threshold. $**p<0.0.5$, compared to sham group.
Figure 5:
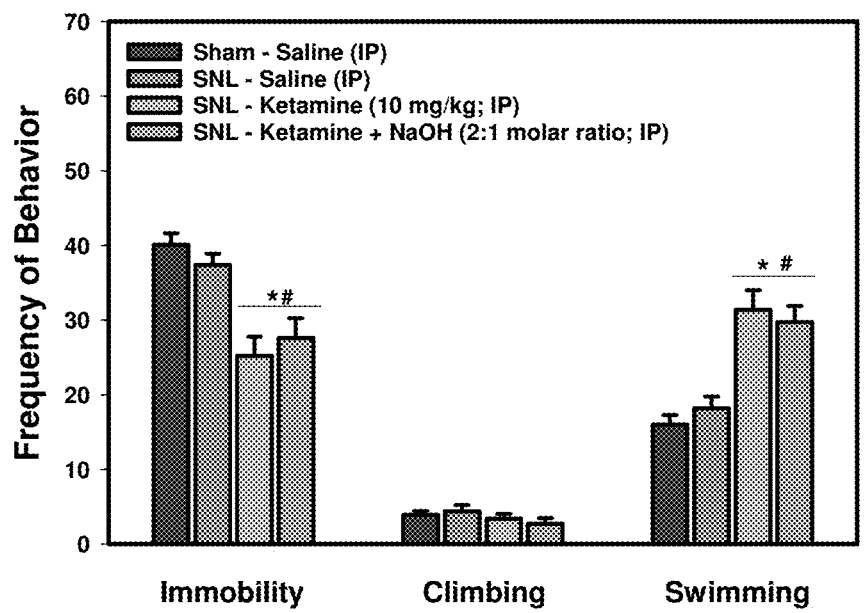
FIG. 5 compares the results of SNL animals in the forced swim test. The same test groups as In FIG. 4 are shown. Immobility, climbing, and swimming are shown. Decreased immobility and increased swimming are indicative of an antidepressant effect. $*p<0.05$ compared to Sham-Saline; $\#p<0.05$ compared to SNL-Saline.

Results: Pain and anti-depression responses were assessed in 4 groups: Control, SNL alone, SNL+ketamine, and SNL+ketamine NaOH (0.5 ratio). As expected, SNL induced a chronic pain syndrome, as reflected in a significantly reduced paw withdrawal threshold in all SNL groups (FIG. 4). Both ketamine and ketamine NaOH significantly reduced immobility time and increased swimming time in SNL animals, with numerically greater effects of ketamine NaOH (FIG. 5).

Conclusions: Effects of ketamine on the FST have been most extensively documented in non-perturbed animals. The degree to which these effects are maintained in animals with SNPL induced chronic pain has not previously been examined. Here we demonstrate anti-depressant efficacy of the ketamine-NaOH combination in animals with documented chronic pain.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

The invention claimed is:

1. A pharmaceutical formulation comprising ketamine and a bitter taste receptor (TAS2R) response mediating agent, wherein the ketamine is racemic ketamine, S-ketamine, or R-ketamine, and is provided at a concentration between 100 µM and 1 mM, inclusive, the TAS2R response mediating agent is NaOH, and wherein the molar ratio of ketamine to NaOH is from 2:1 to 1:1.

2. The pharmaceutical formulation of claim 1, wherein the molar ratio of ketamine to NaOH is 2:1.

3. The pharmaceutical formulation of claim 1, wherein the formulation is formulated for parenteral administration.

4. The pharmaceutical formulation of claim 3, wherein the formulation is formulated for subcutaneous, intramuscular, intravenous, intraarticular, intraperitoneal, or intrathecal administration.

5. A method for treatment of chronic pain or chronic pain associated with depression, comprising administering to a subject in need thereof an effective amount of the pharmaceutical formulation of claim 1, thereby treating the chronic pain or chronic pain associated with depression.

6. The method of claim 5, wherein the molar ratio of ketamine to NaOH is 2:1.

7. The method of claim 5, wherein the formulation is administered parenterally.

8. The method of claim 7, wherein the formulation is administered subcutaneously, intramuscularly, intravenously, intraarticularly, intraperitoneally, or intrathecally.

9. The method of claim 5, wherein the formulation is administered as a single bolus, a gradual infusion, or a combination thereof.

10. The method of claim 5, wherein the depression is major depression or bipolar depression.

11. The pharmaceutical formulation of claim 1, wherein the ketamine is provided at a concentration of 1 mM, and the molar ratio of ketamine to NaOH is 2:1.

12. The pharmaceutical formulation of claim 1, wherein the ketamine is provided at a concentration of 1 mM, and the molar ratio of ketamine to NaOH is 3:2.

13. The pharmaceutical formulation of claim 1, wherein the ketamine is provided at a concentration of 1 mM, and the molar ratio of ketamine to NaOH is 1:1.

14. The pharmaceutical formulation of claim 1, wherein the ketamine is provided at a concentration of 500 nM, and the molar ratio of ketamine to NaOH is 2:1.

15. The pharmaceutical formulation of claim 1, wherein the ketamine is provided at a concentration of 500 nM, and the molar ratio of ketamine to NaOH is 3:2.

16. The pharmaceutical formulation of claim 1, wherein the ketamine is provided at a concentration of 500 nM, and the molar ratio of ketamine to NaOH is 1:1.

17. The method of claim 5, wherein treating the chronic pain or chronic pain associated with depression is associated with psychic pain.

18. The method of claim 9, wherein the gradual infusion is over 5-120 minutes.

19. The method of claim 9, wherein the gradual infusion is over 20, 30, or 40 minutes.

20. The method of claim 9, wherein the molar ratio of ketamine to NaOH is 2:1, and the formulation is administered intravenously over 10-120 minutes.

* * * * *